(12) United States Patent
Kondo et al.

(10) Patent No.: US 6,403,774 B1
(45) Date of Patent: Jun. 11, 2002

(54) AZOAMIDINE COMPOUND

(75) Inventors: Suguru Kondo; Seiji Hirose; Kazuo Shiraki, all of Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/955,338

(22) Filed: Sep. 19, 2001

(30) Foreign Application Priority Data

Oct. 4, 2000 (JP) ........................................ 2000-305230

(51) Int. Cl.[7] ........................... C07C 245/04; C08F 4/04
(52) U.S. Cl. ........................................ 534/751; 526/204
(58) Field of Search .......................... 534/751; 526/204

(56) References Cited

U.S. PATENT DOCUMENTS

| 3,914,340 A | * | 10/1975 | Dekking | ..................... 525/267 |
| 4,990,600 A | | 2/1991 | Tanaka et al. | ............... 534/751 |

OTHER PUBLICATIONS

Patent Abstract of Japan, Publication No. JP61065858, dated Apr. 4, 1986.
Patent Abstract of Japan, Publication No. JP63115869, dated May 20, 1988.
Patent Abstract of Japan, Publication No. JP63239260, dated Oct. 5, 1988.

* cited by examiner

*Primary Examiner*—Fiona T. Powers
(74) *Attorney, Agent, or Firm*—Armstrong, Westerman & Hattori, LLP

(57) ABSTRACT

A compound shown by the general formula [1]:

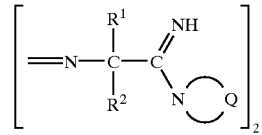

[1]

(Wherein, $R^1$ and $R^2$ are each independently a hydrogen atom, a lower alkyl group or a cyano group, and

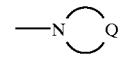

is an optionally substituted heterocyclic compound.); or a salt thereof.

12 Claims, No Drawings

AZOAMIDINE COMPOUND

BACKGROUND OF THE INVENTION

The present invention relates to a useful azoamidine compound as a water soluble polymerization initiator.

In recent years in manufacturing of polymers, studies have been actively conducted how to complete a polymerization in higher concentration in shorter time for pursuing rationalization. In particular, in polymerization in an aqueous solution, polymerization temperature tends to become increasingly higher and polymerization time increasingly shorter year by year. Therefore, use of a conventional polymerization initiator such as redox initiator, persulfate compound, peroxide initiator and azo initiator tends to cause problems such as an increase of the amount of monomer remained by failing to complete the polymerization with due to too high activity of the initiator at the polymerization temperature.

In order to solve this problem, various methods have been studied, for example, by increasing an addition amount of an initiator, by adding an initiator in the middle of the reaction or by using multiple initiators having different activities in combination. However, these methods have still the following problems. The method by increasing an initiator amount has little effect due to decomposition of most of the initiator during polymerization, and the method by adding an initiator in the middle of the reaction also has a problem that the added initiator can not be sufficiently mixed due to an increase of viscosity of the polymerization solution.

And so, further methods have been proposed to solve this problem, for example, by using multiple polymerization initiators each having a different 10 hour half-life temperature corresponding to the temperature elevation range during the polymerization or by using an initiator having a decomposition activity corresponding to the polymerization temperature. However, in the method by using multiple polymerization initiators in combination, for example, the polymerization method using an azoamidine salt type polymerization initiator having a 10 hour half-life temperature of 45 to 60° C. (low temperature activity) and another azoamide salt type polymerization initiator containing hydroxy group and having a 10 hour half-life temperature of 80 to 90° C. (high temperature activity) together, there is still a problem that the polymerization reaction can not be well controlled. As another mean to solve this problem, it is considered to use an initiator having a decomposition activity corresponding to the conventional temperature elevation range (40 to 90° C.), namely, having a 10 hour half-life temperature of 60 to 70° C., however, such an initiator has not been found yet. Therefore, there is needed to develop a water soluble azo type polymerization initiator having a 10 hour half-life temperature of 60 to 70° C.

SUMMARY OF THE INVENTION

The present invention has been conducted based on the present situations as described above. And its object is to provide a novel azoamidine compound having a 10 hour half-time temperature of 60 to 70° C. in water which is useful as a water soluble polymerization initiator and enables to effectively polymerize various monomers in a polymerization in an aqueous solvent.

The present invention relates to a compound shown by the general formula [1]:

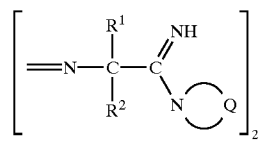

(wherein, $R^1$ and $R^2$ are each independently a hydrogen atom, a lower alkyl group or a cyano group, and

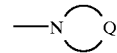

is an optionally substituted heterocyclic compound); or a salt thereof (hereinafter referred to the azoamidine compound of the invention).

The present invention also relates to a polymerization initiator comprising the azoamidine compound of the invention.

The present invention further relates to a method for polymerizing an α,β-ethylenically unsaturated monomer, wherein the azoamidine compound of the invention is used as a polymerization initiator.

The inventors of the present invention have extensively made study to attain the above objects, and found out that the azoamidine compound having a heterocyclic compound such as pyrrolidine ring in the molecule had the 10 hour half-life temperature in water of 60 to 70° C. and its use enabled more effective polymerization in an aqueous solvent than the conventional methods, and thus completed the present invention.

DETAILED DESCRIPTION OF THE PREFERRED EMBODIMENTS

In the general formula [1], the lower alkyl group shown by $R^1$ and $R^2$ may be linear chained, branched or cyclic, and includes a group having from 1 to 5 carbon atoms, preferably from 1 to 3 carbon atoms, and are specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a sec-pentyl group, a 2-methylbutyl group, a 1-ethylpropyl group, a 2-ethylpropyl group, a cyclopropyl group, a cyclobutyl group, a cyclopentyl group etc., and a methyl group is most preferable among others.

A heterocyclic compound which derives an optionally substituted heterocyclic compound shown by the following formula:

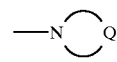

includes a 5-membered or a 6-membered ring compound irrespective of being saturated or unsaturated and having one or more nitrogen atom as a hetero atom, typically from 1 to 3, preferably one, and such a heterocyclic compound may further have typically one oxygen atom. Such a heterocyclic compound includes, for example, a saturated heterocyclic compound such as imidazolidine, pyrrolidine, pyrazolidine, piperidine, piperazine and morpholine; and an unsaturated heterocyclic compound such as pyrrol, pyrroline, imidazole, imidazoline, pyrazole, pyrazoline and triazole etc., among others, saturated heterocyclic compounds such as imidazolidine, pyrrolidine, pyrazolidine, piperidine, piperazine and morpholine are preferable, and pyrrolidine is most preferable.

Such a heterocyclic compound may have further substituents. Such a substituent is one which replaces a hydrogen atom of ring forming —NH— or similarly a hydrogen atom of —CH$_2$— or =CH—, and includes, for example, a lower alkyl group such as a methyl group, an ethyl group and an n-propyl group; a lower alkoxy group such as a methoxy group, an ethoxy group and an n-propoxy group; a halogen atom such as fluorine, chlorine, bromine and iodine etc.

A typical example of the azoamidine compound of the present invention shown by the above general formula [1] includes the followings:

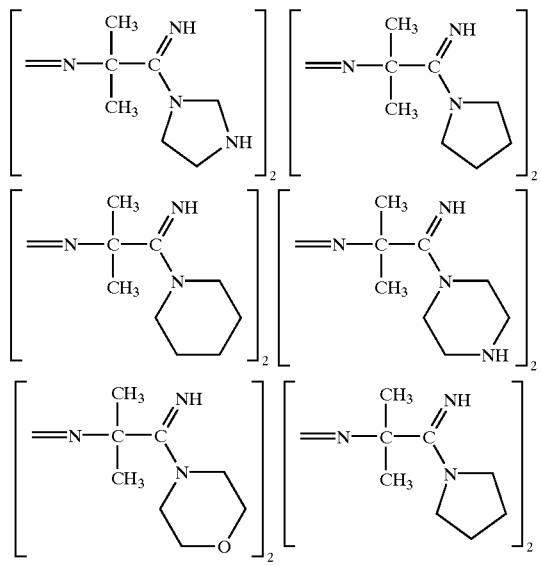

Among which, the following compound is most preferable:

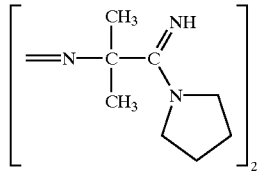

Further, such a typical compound may include a salt thereof. The salt includes one constituted with an inorganic acid such as sulfuric acid, nitric acid, hydrochloric acid and with lower carboxylic acids such as acetic acid, lactic acid and citric acid etc.

The azoamidine compound of the present invention can be prepared by reacting an azodiimino ether compound or a salt thereof shown by the following general formula [2]:

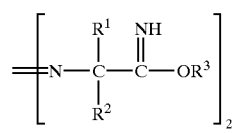

[2]

(wherein, R$^3$ is a lower alkyl group and R$^1$ and R$^2$ are the same as described above); with an amine compound shown by the following general formula [3]:

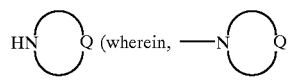

[3]

is the same as described above);
in an appropriate solvent or without any solvent:

In the general formula [2], the lower alkyl group shown by R$^3$ may be linear chained or branched, and includes a group having from 1 to 6 carbon atoms, preferably, from 1 to 4 carbon atoms, and are specifically exemplified by a methyl group, an ethyl group, an n-propyl group, an isopropyl group, an n-butyl group, an isobutyl group, a tert-butyl group, a sec-butyl group, an n-pentyl group, an isopentyl group, a tert-pentyl group, a sec-pentyl group, a neopentyl group, an n-hexyl group, etc.

Typical examples of the azodiimino ether shown by the general formula [2] include, for example,
2,2'-azobis(1-imino-2-methylpropylmethylether),
2,2'-azobis(1-imino-2-methylpropylethylether),
2,2'-azobis(1-imino-2-methylpropyl-n-propylether),
2,2'-azobis(1-imino-2-methylpropylisopropylether),
2,2'-azobis(1-imino-2-methylpropyl-n-butylether),
2,2'-azobis(1-imino-2-ethylpropylmethylether) and
2,2'-azobis(1-imino-2-ethylpropylethylether), etc.

For these azodiimino ethers, a commercial product may be used, or a compound obtained by a conventional method such as a reaction of azobisisobutyronitrile with hydrochloride may be used.

As the amine compound shown by the general formula [3], the same compound corresponding to the heterocyclic amine may be used which enables to derive a heterocyclic compound shown by the following general formula:

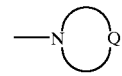

A reaction solvent includes a hydrocarbon such as toluene, xylene, benzene, cyclohexane, n-hexane and n-octane; an alcohol such as methanol, ethanol, n-propanol, isopropanol, n-butanol, isobutanol and tert-butanol; a halogenated hydrocarbon such as carbon tetrachloride, chloroform, methylene chloride, dichloroethane and trichloroethane; a ester such as ethyl acetate, butyl acetate and methyl propionate; dimethyl formamide, dimethyl sulfoxide, water, etc. They may be used alone or in appropriate combination of two or more thereof.

An amount of the amine compound shown by the general formula [3] to be used depends on kinds of the amine compound and the azodiimino ether compound used, and is typically from 1.5 to 10 times by mole, preferably from 2 to 5 times by mole to the azodiimino ether compound.

A reaction temperature is not specifically restricted, but too high temperature decomposes an azo group, whereas too low temperature lowers the reaction rate and a long preparing time is required. Therefore, the reaction temperature is usually from –10 to 40° C., and preferably from 0 to 30° C.

A reaction time depends on kinds of the azodiimino ether compound or the amine compound, but is usually from 1 to 24 hours.

Reaction procedures and post-treatments other than those described above may be in accordance with those in well known similar reactions.

For the azodiimino ether compound shown by the general formula [2] and the salt thereof and the amine compound shown by the general formula [3] used for manufacturing the azoamidine compound shown by the general formula [1] of the present invention, a commercial product or a compound properly prepared by a conventional method may be used.

In thus obtained azoamidine compound of the present invention, its azo group is easily decomposed by heating or irradiation of light to generate radicals along with nitrogen gas, and therefore when various kinds of polymerizable monomers coexist in the system, monomers can rapidly polymerized. The compound is more superior in solubility in water, methanol, and the like compared with known azoamidine compounds, and its 10 hour half-life temperature is 60 to 70° C., therefore, it provides an effective polymerization in an aqueous solvent.

Polymerization or copolymerization of polymerizable monomers using the azoamidine compound of the present invention as a polymerization initiator can be performed by carrying out a polymerization reaction using the azoamidine compound of the present invention and the polymerizable monomer in an appropriate solvent or without solvent, optionally under inert gas atmosphere, in accordance with the conventional method.

The above described polymerizable monomer includes an α,β-ethylenically unsaturated monomer shown by the following general formula [4]:

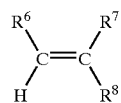

[4]

(wherein, $R^6$ is a hydrogen atom, a lower alkyl group, a carboxyl group, a carboxyalkyl group, an alkyloxycarbonyl group, a hydroxyalkyloxycarbonyl group, a cyano group and an aldehyde group, $R^7$ is a hydrogen atom, a lower alkyl group, a carboxyl group, an alkyloxycarbonyl group, a hydroxyalkyloxycarbonyl group, a cyano group and a halogen atom and $R^8$ is a hydrogen atom, a lower alkyl group, a haloalkyl group, a hydroxyl group, an optionally substituted aryl group, an aliphatic heterocyclic group, an aromatic heterocyclic group, a halogen atom, an alkyloxycarbonyl group, a hydroxyalkyloxycarbonyl group, a sulfonic acid group, a cyano group, a cyanoalkyl group, an acyloxy group, a carboxyl group, a carboxyalkyl group, an aldehyde group, an amino group, an aminoalkyl group, a carbamoyl group, an N-alkylcarbamoyl group and a hydroxyalkyl group. And $R^6$ and $R^7$ may combine each other to form an aliphatic ring together with an adjacent —C=C—).

The lower alkyl group shown by from $R^6$ to $R^8$ in the general formula [4] may be linear chained, branched or cyclic, and includes a group having from 1 to 6 carbon atoms, preferably, from 1 to 4 carbon atoms, and are exemplified by such a methyl group, an ethyl group, an n-propyl group, an isopropyl group, an n-butyl group, an isobutyl group, a tert-butyl group, a sec-butyl group, an n-pentyl group, an isopentyl group, a tert-pentyl group, a 1-methylpentyl group, an n-hexyl group, an isohexyl group, a cyclopropyl group, a cyclopentyl group, a cyclohexyl group, etc.

The caboxyalkyl group shown by $R^6$ and $R^8$ includes, for example, the above lower alkyl groups in which a part of the hydrogen atoms is substituted by a carboxyl group, and typically includes, for example, a carboxymethyl group, a carboxyethyl group, a carboxypropyl group, a carboxybutyl group, a carboxypentyl group, a carboxyhexyl group, etc.

The alkyloxycarbonyl group shown by from $R^6$ to $R^8$ is preferably a group having from 2 to 11 carbon atoms and includes, for example, a methoxycarbonyl group, an ethoxycarbonyl group, a propoxycarbonyl group, butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group, a decyloxycarbonyl group, etc.

The hydroxyalkyloxycarbonyl group shown by from $R^6$ to $R^8$ is the above alkyloxycarbonyl group having from 2 to 11 carbon atoms in which a part of hydrogen atoms is substituted by a hydroxyl group, and includes, for example, a hydroxymethyloxycarbonyl group, a hydroxyethyloxycarbonyl group, a hydroxypropyloxycarb group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group, a hydroxydecyloxycarbonyl group, etc.

The halogen atom shown by $R^7$ and $R^8$ includes fluorine, chlorine, bromine and iodine.

The haloalkyl group shown by $R^8$ includes the above described lower alkyl group substituted by halogen atom(s) (for example, fluorine, chlorine, bromine and iodine) having from 1 to 6 carbon atoms, and are specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group, a 6-chlorohexyl group, etc.

In the optionally substituted aryl group, the aryl group includes a phenyl group, a tolyl group, a xylyl group and a naphtyl group. Said substitutuent includes an amino group, a hydroxyl group, a lower alkoxy group, a carboxyl group, and the substituted aryl group includes, for example, an aminophenyl group, a toluidino group, a hydroxyphenyl group, a methoxyphenyl group, a tert-butoxyphenyl group, a carboxyphenyl group, etc.

The aliphatic heterocyclic group includes preferably a 5-membered or a 6-membered ring heterocyclic group having from 1 to 3 hetero atoms such as a nitrogen atom, an oxygen atom and a sulfur atom, and are specifically exemplified by a pyrrolidyl-2-on group, a pyperidyl group, a pyperidino group, a pyperazinyl group, a morpholino group, etc.

The aromatic heterocyclic group includes preferably a 5-membered or a 6-membered heterocyclic having from 1 to 3 hetero atoms such as nitrogen, oxygen and sulfur atom, and are specifically exemplified by a pyridyl group, an imidazolyl group, a thiazolyl group, a furanyl group, a pyranyl group, etc.

The cyano-containing alkyl group includes the above described lower alkyl in which a part of hydrogen atoms is substituted by a cyano group, and are specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group, a 6-cyanohexyl group, etc.

The acyloxy group includes a group derived from a carboxylic acid having from 2 to 20 carbon atoms, and are specifically exemplified by an acetyloxy group, a propionyloxy group, butyryloxy group, a pentanoyloxy group, a hexanoyloxy group, a heptanoyloxy group, an octanoyloxy group, a nonanoyloxy group, a decanoyloxy group, a benzoyloxy group, etc.

The aminoalkyl group includes the above described lower alkyl group in which a part of hydrogen atoms is substituted by an amino group, and are specifically exemplified by an aminomethyl group, an aminoethyl group, an aminopropyl group, an aminobutyl group, an aminopentyl group, an aminohexyl group, etc.

The N-alkylcarbamoyl group includes carbamoyl group in which a part of hydrogen atoms is substituted by an alkyl group, and are specifically exemplified by an N-methylcarbamoyl group, an N-ethylcarbamoyl group, an N-n-propylcarbamoyl group, an N-isopropylcarbamoyl group, an N-n-butylcarbamoyl group, an N-t-butylcarbamoyl group, etc.

The hydroxyalkyl group is the above described lower alkyl group in which a part of hydrogen atoms is substituted by a hydroxyl group, and are specifically exemplified by a hydroxymethyl group, a hydroxyethyl group, a hydroxypropyl group, a hydroxybutyl group, a hydroxypentyl group, a hydroxyhexyl group, etc.

The aliphatic ring formed by linking $R^6$ and $R^7$ together with an adjacent —C=C— includes an unsaturated aliphatic ring having from 5 to 10 carbon atoms, which may be monocyclic or polycyclic. The ring includes, for example, a norbornene ring, a cyclopentene ring, a cyclohexene ring, a cyclooctene ring, a cyclodecene ring, etc.

The specific examples of the α,β-ethylenically unsaturated monomer shown by the general formula [4] are halogen-containing ethylenically unsaturated aliphatic hydrocarbons having from 2 to 20 carbon atoms such as ethylene, propylene, butylene and isobutylene; ethylenically unsaturated aromatic hydrocarbons having from 8 to 20 carbon atoms such as styrene, 4-methylstyrene, 4-ethylstyrene and divinylbenzene; alkenyl esters having from 3 to 20 carbon atoms such as vinyl formate, vinyl acetate, vinyl propionate and isopropenyl acetate; halogenated ethylenically unsaturated compounds having from 2 to 20 carbon atoms such as vinyl chloride, vinylidene chloride and vinylidene fluoride; ethylenically unsaturated carboxylic acids having from 3 to 20 carbon atoms such as acrylic acid, methacrylic acid, itaconic acid, maleic acid, fumaric acid, crotonic acid, vinylacetic acid, allylacetic acid and vinylbenzoic acid (each of these acids may be in the form of a salt, for example, an alkali metal salt such as a sodium and a potassium salt, an ammonium salt or the like); ethylenically unsaturated carboxylic acid esters having from 4 to 20 carbon atoms such as methyl methacrylate, ethyl methacrylate, propyl methacrylate, butyl methacrylate, 2-ethylhexyl methacrylate, stearyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenate; cyano-containing ethylenically unsaturated compounds having from 3 to 20 carbon atoms such as acrylonitrile, methacrylonitrile and allyl cyanide; ethylenically unsaturated amide compounds having from 3 to 20 carbon atoms such as acrylamide and methacrylamide; ethylenically unsaturated aldehydes having from 3 to 20 carbon atoms such as acrolein and crotonaldehyde; ethylenically unsaturated sulfonic acids having from 2 to 20 carbon atoms such as vinyl sulfonic acid and 4-vinylbenzene sulfonic acid; ethylenically unsaturated aliphatic amines having from 2 to 20 carbon atoms such as vinyl amine and allyl amine (each of these acids may be in the form of a salt, for example, an alkali metal salt such as a sodium and a potassium salt); ethylenically unsaturated aromatic amines having from 8 to 20 carbon atoms such as vinyl aniline; ethylenically unsaturated aliphatic heterocyclic amines having from 5 to 20 carbon atoms such as N-vinyl pyrrolidone and vinyl piperidine; ethylenically unsaturated aromatic heterocyclic amines having from 5 to 20 carbon atoms such as vinyl pyridine and 1-vinylimdazole; ethylenically unsaturated alcohols having from 3 to 20 carbon atoms such as allyl alcohol and crotyl alcohol; ethylenically unsaturated phenols having from 8 to 20 carbon atoms such as 4-vinyl phenol, etc.

A compound other than the azoamidine compound of the present invention may be used as a polymerization initiator together with the azoamidine compound of the present invention. The polymerization initiator other than the azoamidine compound to be used in combination includes an azo compounds such as 2,2'-azobisisobutyronitrile, 2,2'-azobis (2,4-dimethyl valeronitrile), 2,2'-azobis(2-amidinopropane) .dihydrochloride, 2,2'-azobis(2-methylpropionamidine) .dihydrochloride, 2,2'-azobis[2-(2-imidazoline-2-il) propane], 2,2'-azobisisobutylamide.dihydrate, dimethyl 2,2'-azobis(2-methylpropionate) and 4,4'-azobis(4-cyanovaleric acid); along with redox type polymerization initiators such as benzoyl peroxide and di-tert-butyl peroxide; and photo polymerization initiators such as benzoin ethyl ether, benzoin isopropyl ether and benzyl dimethyl ketal.

The polymerization method includes, for example, solution polymerization, bulk polymerization, suspension polymerization, emulsion polymerization, etc.

A solvent used in the solution polymerization includes ethers such as tetrahydrofuran, diethyl ether and dioxane; alcohols such as methanol, ethanol and isopropanol; N,N-dimethyl formamide, dimethyl sulfoxide, water, etc. Such a solvent may be used alone or in proper combination of two or more thereof.

In an emulsion polymerization, a surfactant commonly used in this field may be used.

The polymerization reaction is preferably performed under inert gas atmosphere. The inert gas includes, for example, nitrogen gas, argon gas and the like.

An amount of the azoamidine compound of the present invention used as a polymerization initiator depends on kinds of polymerizable monomer used, but when the azoamidine compound of the present invention is used alone, it is usually from 0.01 to 100 wt %, preferably from 0.05 to 50 wt % based on the polymerizable monomer. When the azoamidine compound of the present invention and other polymerization initiators are used in combination, the ratio may be selected properly taking kinds of the polymerization initiator and the polymerizable monomer and intended property of a resulting polymer etc. into consideration.

Concentration of the polymerizable monomer during polymerization reaction depends on kinds of the polymerizable monomer, but it is usually from 5 to 100 wt % (no solvent), preferably from 10 to 60 wt %.

The polymerization temperature is not specifically restricted, however, too low temperature retards process of the polymerization due to less decomposition of the azo group, whereas too high temperature causes too much decomposition of the azo group because of making control of the polymerization difficult. Therefore the temperature is usually from 20 to 150° C., and preferably from 30 to 100° C. When the polymerization reaction is performed in an aqueous solvent, the reaction temperature is preferably from 30 to 100° C. In this case, the aqueous solvent includes water, water-methanol mixture, water-ethanol mixture, methanol, ethanol, etc. Among them, water is preferable.

A polymerization reaction time depends on reaction conditions such as a polymerization temperature and kinds or concentration of a polymerizable monomer to be reacted and the azoamidine compound of the present invention to be used, and it is usually from 2 to 24 hours.

The azoamidine compound of the present invention is superior in solubility in water or methanol compared with the known azoamidine compounds, and has 10 hour half-life temperature of from 60 to 70° C. which is never seen before. Therefore, the compound can provide an effective polymerization reaction in an aqueous solvent by using as a polymerization initiator, and further enables easy temperature control when it used with other polymerization initiators in combination.

The present invention is explained further in detail using the following Examples and Comparative Examples, and the present invention should not be restricted by them.

EXAMPLE

Example 1

A suspension consisting of 60 g of azobisisobutyronitrile, 28 g of methanol and 270 ml of toluene was reacted by introducing 32 g of hydrogen chloride to obtain a toluene suspension of 2,2'-azobis (1-imino-1-methoxy-2-methylpropane) hydrochloride. To the toluene suspension was added 62 g of pyrrolidine, and reacted at room temperature for 7 hours. After standing overnight, crystals were filtered and dried to get 50 g of pale yellow crystal of 2,2'-azobis[2-methyl-1-(1-pyrrolidinyl)iminopropane] hydrochloride.

mp: 172° C. (decomposition)

1 H-NMR δ ppm (CD$_3$OD): 1.53 (12H, s, —CH$_3$), 1.95 (8H, β-pyrrolidine ring), 3.50 (8H, m, α-pyrrolidine ring), 4.8 ppm (4H, br, =N—H, HCl)

UV: λ max 373 nm (E1%=0.838/CH$_3$OH) 10 hour half-life temperature: 66.5° C.

Decomposition rate constant k60° C.=7.94×10$^{-6}$(sec$^{-1}$)

lnA=34.19 k70° C.=3.03×10$^{-5}$(sec$^{-1}$)

Ea=30.39(kcal/mol)

Example 2

A suspension consisting of 60 g of azobisisobutyronitrile, 28 g of methanol and 270 ml of toluene was reacted by introducing 32 g of hydrogen chloride to obtain a toluene suspension of 2,2'-azobis(1-imino-1-methoxy-2-methylpropane) hydrochloride. The toluene suspension was neutralized with ammonia, followed by filtering to obtain a toluene solution of 2,2'-azobis(1-imino-1-methoxy-2-methylpropane). To the toluene solution was added 62 g of pyrrolidine, and reacted for 7 hours. After standing overnight, ethyl acetate was poured into the reaction solution, and crystals ware filtered and dried to obtain 10 g of pale yellow crystal of 2,2'-azobis [2-methyl-1-(N-pyrrolidinyl)iminopropane].

1 H-NMR δ ppm (CD$_3$OD): 1.52 (12H, s, —CH$_3$), 1.95 (8H, m, β-pyrrolidine ring), 3.50 (8H, m, α-pyrrolidine ring), 4.7 ppm (2H, br, =N—H)

Example 3

In 378 g of distilled water, 20 g of acrylamide was dissolved, followed by heating to 70° C. under nitrogen atmosphere and charging with 2 ml of an aqueous solution of the azoamidine compound obtained in Example 1 (0.019 mol/L), was polymerized at 70° C. A part of the reaction solution was collected as a sample at each specified interval. Methanol was added to the reaction solution as a sample to precipitate and separate a polymer, followed by drying the polymer to determine the polymerization rate at each time. Results are shown in Table 1.

Comparative Example 1

The same procedures as in Example 3 were performed to determine the polymerization rate except that a typical conventional azoamidine compound, 2,2'-azobis(2-methylpropionamidine) hydrochloride (hereinafter abbreviated as Comparative Compound 1) was used instead of azoamidine hydrochloride obtained in Example 1. Results are also shown in Table 1.

Comparative Example 2

The same procedures as in Example 3 were performed to determine polymerization rate except that a typical conventional azoamidine compound, 2,2'-azobis[N-(2-hydroxyethyl)-2-methylpropionamide] (hereinafter abbreviated as Comparative Compound 2) was used instead of azoamidine hydrochloride obtained in Example 1. Results are also shown in Table 1.

TABLE 1

| Polymerization Time | Rate of Polymerization (%) of Compound obtained in Example 2 | Rate of Polymerization (%) of Comparative Compound 1 | Rate of Polymerization (%) of Comparative Compound 2 |
| --- | --- | --- | --- |
| 0.5 H | 25.7 | 59.9 | 11.5 |
| 1 H | 59.0 | 70.7 | 18.5 |
| 1.5 H | 67.0 | 76.5 | 24.5 |
| 2 H | 72.7 | 76.8 | 30.5 |
| 3 H | 78.3 | 76.3 | 41.4 |
| 4 H | 85.8 | 75.8 | 54.0 |
| 5 H | 89.3 | 76.5 | 63.5 |
| 6 H | 87.8 | 76.2 | 71.0 |

As clearly shown in Table 1, when polymerization is carried out at 70° C., the azoamidine compound of the present invention gives a higher polymerization rate by 10 or more % compared with those of the conventional Comparative Compounds 1 and 2 in the polymerization time over 4 hours.

Effects of Invention

As described above, the present invention provides a novel azoamidine compound having superior solubility in such a solvent as water and methanol. In addition, said azoamidine compound also has 10 hour half-life temperature of from 60 to 70° C. in water, therefore, it enables to effectively polymerize various monomers when it is used as a polymerization initiator in a polymerization in an aqueous solvent.

This patent application is based upon Japanese Patent Application No.2000-305230.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound shown by the general formula [1]:

$$\left[ =N-\underset{R^2}{\overset{R^1}{\underset{|}{C}}}-\overset{NH}{\underset{N\frown Q}{C}} \right]_2 \quad [1]$$

wherein, $R^1$ and $R^2$ are each independently a hydrogen atom, a lower alkyl group or a cyano group, and $$-N\frown Q$$

is an optionally substituted heterocyclic group; or a salt thereof, wherein the optionally substituted heterocyclic group is an unsubstituted heterocyclic group, or a heterocyclic group substituted by a lower alkyl group, a lower alkoxy group and/or a halogen atom.

2. The compound according to claim 1, wherein the heterocyclic group is one of a 5-membered ring and a 6-membered ring.

3. The compound according to claim 1, wherein the heterocyclic group contains from 1 to 3 nitrogen atoms in the ring.

4. The compound according to claim 1, wherein the heterocyclic group is a saturated heterocyclic group.

5. A compound shown by the general formula [1]:

$$\left[ =N-\underset{R^2}{\overset{R^1}{\underset{|}{C}}}-\overset{NH}{\underset{N\frown Q}{C}} \right]_2 \quad [1]$$

wherein, $R^1$ and $R^2$ are each independently a hydrogen atom, a lower alkyl group or a cyano group, and $$-N\frown Q$$

is an optionally substituted heterocyclic group; or a salt thereof, wherein the optionally substituted heterocyclic group is 1-pyrrolidinyl.

6. The compound according to claim 1, wherein the lower alkyl group shown by $R^1$ and $R^2$ is each independently an alkyl group having from 1 to 5 carbon atoms.

7. The compound according to claim 5, wherein both $R^1$ and $R^2$ are a methyl group.

8. A compound shown by the general formula [1]:

$$\left[ =N-\underset{R^2}{\overset{R^1}{\underset{|}{C}}}-\overset{NH}{\underset{N\frown Q}{C}} \right]_2 \quad [1]$$

wherein, $R^1$ and $R^2$ are each independently a hydrogen atom, a lower alkyl group or a cyano group, and $$-N\frown Q$$

is an optionally substituted heterocyclic group; or a salt thereof, wherein the compound is one selected from the group consisting of the following 6 formulae and salts thereof:

$$\left[ =N-\underset{CH_3}{\overset{CH_3}{\underset{|}{C}}}-\overset{NH}{\underset{N\frown NH}{C}} \right]_2$$

$$\left[ =N-\underset{CH_3}{\overset{CH_3}{\underset{|}{C}}}-\overset{NH}{\underset{N\frown}{C}} \right]_2$$

$$\left[ =N-\underset{CH_3}{\overset{CH_3}{\underset{|}{C}}}-\overset{NH}{\underset{N\frown}{C}} \right]_2$$

$$\left[ =N-\underset{CH_3}{\overset{CH_3}{\underset{|}{C}}}-\overset{NH}{\underset{N\frown NH}{C}} \right]_2$$

-continued

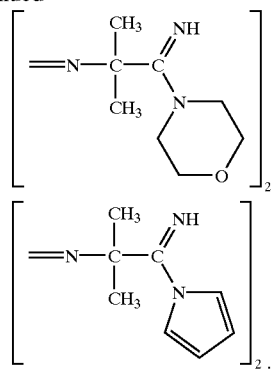

9. A compound shown by the general formula [1]:

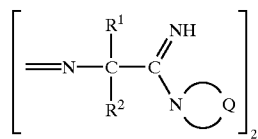

wherein, $R^1$ and $R^2$ are each independently a hydrogen atom, a lower alkyl group or a cyano group, and

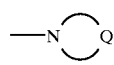

is an optionally substituted heterocyclic group; or a salt thereof, wherein the compound is the following formula or a salt thereof:

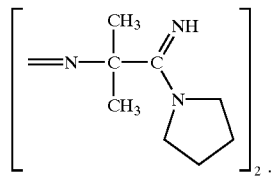

10. A polymerization initiator comprising the compound shown by the general formula [1]:

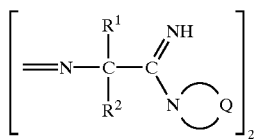

wherein, $R^1$ and $R^2$ are each independently a hydrogen atom, a lower alkyl group or a cyano group, and

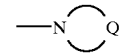

is an optionally substituted heterocyclic group; or a salt thereof, wherein the optionally substituted heterocyclic group is an unsubstituted heterocyclic group, or a heterocyclic group substituted by a lower alkyl group, a lower alkoxy group and/or a halogen atom.

11. A method for polymerizing an α,β-ethylenically unsaturated monomer, wherein the compound shown by the following general formula [1] or the salt thereof is used as a polymerization initiator:

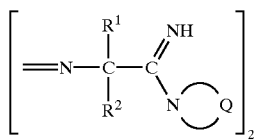

wherein, $R^1$ and $R^2$ are each independently a hydrogen atom, a lower alkyl group or a cyano group, and

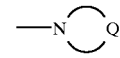

is an optionally substituted heterocyclic group, wherein the optionally substituted heterocyclic group is an unsubstituted heterocyclic group, or a heterocyclic group substituted by a lower alkyl group, a lower alkoxy group and/or a halogen atom.

12. The method according to claim 11, further wherein the polymerizing reaction is performed in an aqueous solvent at 30 to 100° C.

* * * * *